United States Patent [19]

Marlett

[11] Patent Number: 4,588,843
[45] Date of Patent: May 13, 1986

[54] SYNTHESIS OF (ALKOXYALKYL) AMINES

[75] Inventor: Everett M. Marlett, Baton Rouge, La.

[73] Assignee: Ethyl Corporation, Richmond, Va.

[21] Appl. No.: 603,966

[22] Filed: Apr. 26, 1984

[51] Int. Cl.$^4$ ............................................. C07C 93/04
[52] U.S. Cl. ..................................... 564/508; 564/503
[58] Field of Search ................................. 564/508, 503

[56] References Cited

U.S. PATENT DOCUMENTS 3,480,675 11/1969 Poppelsdorf ..................... 564/508

OTHER PUBLICATIONS

Fakstrop et al., "Bifunctional Amines and Ammonium Compounds" Acta Chemica Scand. 7 (1953), pp. 134–139.

Surrey, "Name Reactions in Organic Chemistry" Academic Press Inc. NY (1954), pp. 169–170.

Primary Examiner—Paul F. Shaver
Attorney, Agent, or Firm—John F. Sieberth; Donald L. Johnson

[57] ABSTRACT

It has been discovered that when reaction is effected between an alkali metal omega-amino-alkoxide and an alkyl halide, nucleophilic attack of the alkoxide on the alkyl halide occurs so that an (alkoxyalkyl)amine is formed. The conventional Hofmann displacement reaction (elimination of $CH_3Br$) does not occur to any significant extent. Nor does the common olefin elimination reaction occur to any significant extent when using alkali metal omega-aminoalkoxides having one or two $C_2$ or higher alkyl substituents on the nitrogen atom.

13 Claims, No Drawings

SYNTHESIS OF (ALKOXYALKYL) AMINES

This invention involves the discovery, inter alia, that when reaction is effected between an alkali metal omega-aminoalkoxide and an alkyl halide, nucleophilic attack of the alkoxide on the alkyl halide occurs so that an (alkoxyalkyl)amine is formed. (These products may also be referred to as (alkyl) (omega-aminoalkyl) ethers.)

For example when a sodium or potassium omega-N,N-dialkylaminoalkoxide such as sodium 2-(dimjethylamino)ethoxide is reacted with an alkyl halide such as dodecyl bromide, N-(2-dodecyloxyethyl)dimethylamine is formed in good yield:

$$NaOC_2H_4N(CH_3)_2 + C_{12}H_{25}Br \rightarrow C_{12}H_{25}OC_2H_4N(CH_3)_2 + NaBr$$

The conventional Hofmann displacement reaction (elimination of $CH_3Br$) does not occur to any significant extent.

Nor does the common olefin elimination reaction occur to any significant extent when using alkali metal omega-aminoalkoxides having one or two $C_2$ or higher alkyl substituents on the nitrogen atom.

The alkali metal omega-aminoalkoxides used in the process of this invention may be omega-aminomonoalkoxides, $R^1R^2N-R-O-M$; omega-aminodialkoxides, $R^1N(-R-O-M)_2$; or omega-aminotrialkoxides, $N(-R-O-M)_3$, $R^1$ and $R^2$ being hydrogen or alkyl (e.g., $C_1$ to $C_{24}$, preferably $C_1$ to $C_{18}$, most preferably methyl), R being alkylene of 2 or more carbon atoms (preferably dimethylene, trimethylene, or their higher straight chain homologs) and M being alkali metal (preferably sodium or potassium). The alkali metal omega-aminomonoalkoxides, $R^1R^2N-R-O-M$, may be the alkoxide derivatives of primary, secondary or tertiary alkanol amines, i.e., both of $R^1$ and $R^2$ may be hydrogen (primary alkanol amine), one of $R^1$ may be hydrogen and the other alkyl (secondary alkanol amine) or both of $R^1$ and $R^2$ may be alkyl (tertiary alkanol amine). By the same token the omega-aminodialkoxides, $R^1N(-R-O-M)_2$, may be secondary ($R^1$=hydrogen) or tertiary ($R^1$=alkyl). Thus a variety of different (alkyl) (omega-aminoalkyl) ethers may be produced depending on the kind of such aminoalkoxide employed:

$$R^1R^2N-R-O-M + R^3X \rightarrow R^3O-R-NR^1R^2$$

or $$R^1N(-R-O-M)_2 + 2R^3X \rightarrow (R^3O-R-)_2NR^1$$

or $$N(-R-O-M)_3 + 3R^3X \rightarrow (R^3O-R-)_3N$$

In the above equations $R^3$ represents an alkyl group. In this connection, any alkyl halide co-reactive with the alkali metal omega-aminoalkoxide may be used in the process. The alkyl chlorides and alkyl bromides are preferred, however. The alkyl group may be straight chain or branched chain, and may be primary, secondary or tertiary. The number of carbon atoms in the alkyl group is largely a matter of choice. For producing long chain (alkoxyalkyl)amines for such uses as detergent-dispersants for crankcase lubricating oils, alkyl chlorides or bromides made from oligomeric polyethylenes, oligomeric polypropylenes and oligomeric polyisobutylenes having 100 or more carbon atoms may be used in the process. On the other hand, shorter chain alkyl halides (e.g., $C_8$ to $C_{18}$) will normally be employed when producing (alkoxyalkyl)amines for such uses as surface active agents, foam stabilizers and the like. For such utilities, use of primary $C_8$ to $C_{18}$ alkyl chlorides or bromides is particularly preferred. Even shorter chain alkyl chlorides and bromides (e.g., $C_1$ to $C_8$) yield products of interest for example as agricultural chemicals and intermediates therefor.

It is contemplated that the process of this invention should proceed well when utilizing in lieu of alkyl halides cycloalkyl halides (e.g., cyclopropyl chloride or bromide, cyclopentyl chloride or bromide, cyclohexyl chloride or bromide, etc.), aralkyl halides (e.g., benzyl chloride or bromide, phenethyl chloride or bromide, etc.), alkenyl halides (e.g., vinyl chloride or bromide, allyl chloride or bromide, methallyl chloride or bromide, etc.), and other like substances.

As the above equations indicate, the alkali metal omega-aminalkoxides used in the process may be collectively represented by the general formula $$(R^1)_nN(-R-O-M)_m$$

where $R^1$, R and M are as defined above, n is an integer from zero to 2, m is an integer from 1 to 3, and the total of n and m is 3.

It will of course be understood and appreciated that mixtures of either or both of the reactants (i.e., the alkali metal omega-aminoalkoxide reactant and the alkyl halide reactant) may be used, if desired.

The proportions of the reactants and reaction conditions may be varied to a considerable extent. For example, either reactant may be present in substantial excess over the stoichiometric amount indicated by the above equations. Reaction will proceed at suitable reaction rates at temperatures falling within the range of about 30° to about 250° C. although temperatures outside this range may be used. The reaction may be performed in an inert solvent (e.g., hydrocarbons, ethers, etc.) although this is not necessary.

A preferred embodiment of this invention involves preforming the alkali metal omega-aminoalkoxide prior to conducting the reaction with the alkyl halides. The process of this embodiment comprises reacting an alkanolamine $$(R^1)_nN(-R-OH)_m$$

(where R, $R^1$, m, and n are as above defined) with a strong alkali metal base and thereafter reacting an alkyl halide with the product so formed so that an (alkoxyalkyl)amine is formed. It can thus be seen that monoalkanolamines, dialkanolamines and trialkanolamines may be used in this process. The monoalkanolamines, $R^1R^2N-R-OH$, may be primary ($R^1$ and $R^2$ are both hydrogen), secondary ($R^1$ is hydrogen and $R^2$ is alkyl), or tertiary ($R^1$ and $R^2$ are both alkyl). Likewise, the dialkanolamines, $R^1N(-R-OH)_2$, may be secondary ($R^1$ is hydrogen) or tertiary ($R^1$ is alkyl). Any strong alkali metal base that will form the alkoxide may be used, such as sodium oxide, potassium oxide, sodium hydroxide, potassium hydroxide, and the like. NaOH and KOH are preferred because of their low cost, good reactivity and ready availability.

Preferably the reaction between the alkanol amine and the strong alkali metal base (e.g., NaOH, KOH, etc.) is performed at a temperature within the range of from about 30° to about 150° C. whereas the reaction between the product so formed and alkyl halide (preferably a primary alkyl chloride or bromide) is performed at a temperature within the range of from about 50° to about 250° C. Other temperature conditions may prove useful, however.

This invention will be still further apparent from the following illustrative example.

EXAMPLE

Twenty-four grams (0.6 mole) of sodium hydroxide was dissolved in 133 g (1.5 mole) of N,N-dimethylethanolamine contained in a 500 mL flask while the mixture was being agitated and heated to reflux (ca. 135° C.). Then 37.5 g (0.15 mole) of 1-bromododecane was introduced through a tube extending below the surface of the stirred mixture over a 1.5-hour period at reflux temperature, and heating continued for 2 hours more. Upon cooling, the product was added to 500 mL of water and extracted with 125 mL of ether. The ether layer was washed with 75 mL of water and dried over Na$_2$SO$_4$. The ether solvent was distilled out at atmospheric pressure and the product fractionated under vacuum Three cuts were taken—the first collected at 60°–110° C. at 20 mm Hg weighed 4.3 g, the second obtained at 110°–125° C. at 15 mm Hg weighed 8.5 g and the product cut was collected at 125°–127° C. at 15 mm Hg and weighed 14.3 g. The product cut was found by IR and NMR analysis to be N-(2-dodecyloxyethyl)-dimethylamine, i.e., the dodecyl ether of N,N-dimethylethanolamine (C$_{12}$H$_{25}$OC$_2$H$_4$N(CH$_3$)$_2$). The yield, based only on the purified product cut, was 37%.

This invention enables the production of products having a wide variety of uses. For example, the practice of this invention enables the manufacture of products which may be used either directly as or as intermediates for lubricating oil additives such as detergent-dispersants and pour point depressants, soap and detergent products such as surface active agents and foam stabilizers, extenders for polymers such as polyurethanes and epoxy resins, agricultural chemicals such as herbicides, fungicides, plant growth regulators, insecticides, vermicides, miticides, and the like. See for example Journal of the American Oil Chemists' Society, Volume 51, No. 7, July 1974, pages 385–388; and Hayashi and Kunitomo Japanese No. 48/16161, May 19, 1973 (to Chugai Pharmaceutical Company, Ltd.).

What is claimed is:

1. A process which comprises reacting an alkanolamine with an alkali metal oxide or hydroxide base and thereafter reacting an alkyl halide with the product so formed so that an (alkoxyalkyl)amine is formed.

2. A process of claim 1 wherein the alkyl halide is an alkyl chloride or alkyl bromide.

3. A process of claim 1 wherein the alkyl halide is a primary alkyl chloride or bromide in which the alkyl group contains from about 8 to about 18 carbon atoms.

4. A process of claim 1 in which both said reactions are conducted at a temperature within the range of from about 30° to about 250° C.

5. A process of claim 1 in which said alkanol amine is a primary alkanol amine.

6. A process of claim 1 in which said alkanol amine is a secondary alkanol amine.

7. A process of claim 1 in which said alkanol amine is a tertiary alkanol amine.

8. A process of claim 7 wherein the tertiary alkanol amine is an N,N-dialkylalkanol amine.

9. A process of claim 7 wherein the tertiary alkanol amine is N,N-dimethylethanol amine.

10. A process which comprises reacting an alkanolamine with sodium hydroxide or potassium hydroxide at a temperature within the range of from about 30° to about 150° C. and thereafter introducing into the reaction mixture and reacting in the same reaction vessel a primary alkyl chloride or bromide at a temperature within the range of from about 50° to about 250° C. with the product so formed so that an (alkoxyalkyl)amine is formed.

11. A process of claim 10 wherein the alkanol amine is a tertiary alkanol amine.

12. A process of claim 10 wherein the alkanol amine is an N,N-dialkylalkanol amine.

13. A process of claim 10 wherein the alkanol amine is N,N-dimethylethanol amine.

* * * * *